United States Patent
Jamison et al.

(10) Patent No.: US 6,323,176 B1
(45) Date of Patent: Nov. 27, 2001

(54) CYCLIC PEPTIDE ANTIFUNGAL AGENTS

(75) Inventors: James Andrew Jamison; Michael John Rodriguez; Venkatraghavan Vasudevan, all of Indianapolis, IN (US)

(73) Assignee: Eli Lilly and Company

( * ) Notice: Subject to any disclaimer, the term of this patent is extended or adjusted under 35 U.S.C. 154(b) by 0 days.

(21) Appl. No.: 09/245,572

(22) Filed: Feb. 5, 1999

Related U.S. Application Data

(60) Provisional application No. 60/075,882, filed on Feb. 25, 1998.

(51) Int. Cl.[7] .......................... A61K 38/00; A61K 38/12; C07K 7/00; C07K 7/56
(52) U.S. Cl. .................... 514/7; 514/8; 514/9; 530/317; 530/322
(58) Field of Search ................ 514/7, 8, 9; 530/317, 530/322

(56) References Cited

U.S. PATENT DOCUMENTS

| | | | |
|---|---|---|---|
| 5,366,880 | * | 11/1994 | Schwartz et al. ............. 435/119 |
| 5,854,212 | | 12/1998 | Balkovec et al. ............. 530/317 |

FOREIGN PATENT DOCUMENTS

| | | | |
|---|---|---|---|
| 0 744 405 | | 11/1996 | (EP) . |
| 0744405 | * | 11/1996 | (EP) ........................ C07K/7/56 |
| 97/27864 | | 8/1997 | (WO) . |
| 9727864 | * | 8/1997 | (WO) ........................ A61K/38/12 |

OTHER PUBLICATIONS

Balkovec et al. (1992) "Synthesis, stability, and biological evaluation of water–soluble prodrugs of a new echinocandin lipopeptide. Discovery of a potential clinical agent for the treatment of systemic candidiasis and *Pneomocystis carinii* Pneumonia (PcP)" *J. Med. Chem* 35:194–198.

Turner et al. (1996) "Recent advances in the medicinal chemistry of antifungal agents" *Curr Pharm Des* 2:209–224.

Search report on related European patent application No. 99 30 1315.

* cited by examiner

Primary Examiner—Avis M. Davenport
(74) Attorney, Agent, or Firm—Morrison & Foerster LLP

(57) ABSTRACT

The present invention relates to compounds of formula

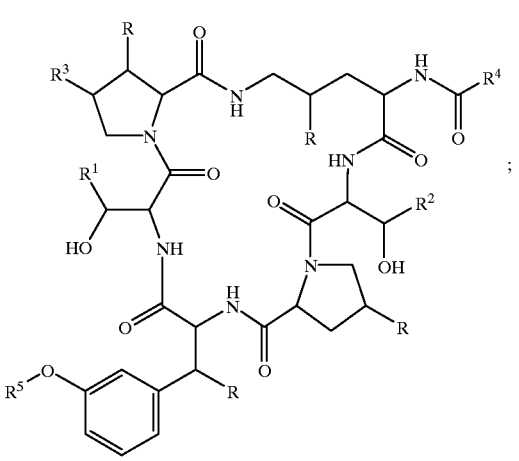

I where $R^5$ is a sugar moiety. The compounds are useful in inhibiting fungal and parasitic activity and infections.

6 Claims, No Drawings

CYCLIC PEPTIDE ANTIFUNGAL AGENTS

This application claims the benefit of U.S. Provisional Application No. 60/075,882 filed Feb. 25, 1998.

FIELD OF THE INVENTION

The present invention relates to anti-fungal/anti-parasitic agents, in particular, derivatives of Echinocandin compounds and their use in the treatment of fungal and parasitic infections.

BACKGROUND OF THE INVENTION

A number of naturally occurring cyclic peptides are known in the art including echinocandin B (A30912A), aculeacin, mulundocandin, sporiofungin, L-671,329, and S31794/F1. In general, these cyclic peptides may be structurally characterized as a cyclic hexapeptide core (or nucleus) with an acylated amino group on one of the core amino acids. This acyl group is typically a fatty acid moiety forming a side chain off the nucleus. For example, echinocandin B has a linoleoyl side chain while aculeacin has a palmitoyl side chain.

These natural products have limited inherent antifungal and antiparasitic properties. The natural compounds may be structurally modified in order to enhance these properties or to improve the compound's stability and/or water solubility. Turner, W. W., Rodriguez, M. J., *Cur. Pharm. Des.*, 2:209, 1996. For example, the fatty acid side chain may be removed from the cyclic peptide core to provide an amino nucleus which may then be re-acylated to provide semi-synthetic compounds. Furthermore, the homotyrosine moiety in the cyclic peptide may be O-glycosylated to provide further elaborated, novel, semi-synthetic compounds such as those claimed in the present application.

BRIEF SUMMARY OF THE INVENTION

This invention relates to compounds of formula I:

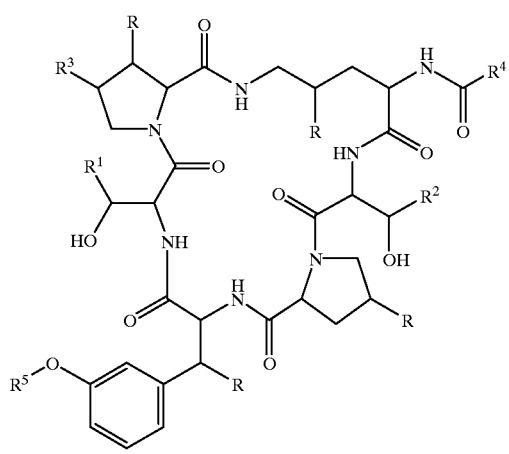

where:

R is independently at each occurrence hydrogen, hydroxy, or O—Pg;

$R^1$ is hydrogen, methyl, $CH_2C(O)NH_2$, $CH_2C(O)NH$—Pg;

$R^2$ and $R^3$ are independently hydrogen or methyl;

$R^4$ is a moiety of the formula:

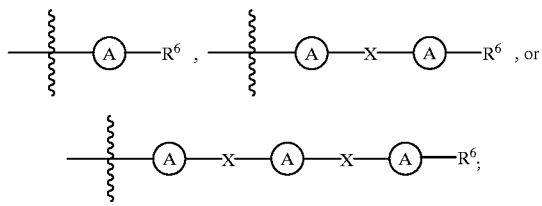

$R^5$ is a moiety of the formula:

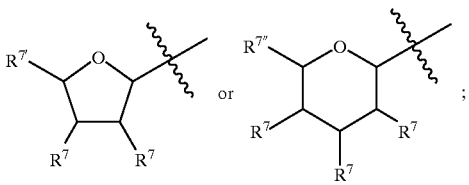

A is independently at each occurrence phen-di-yl, pyridin-di-yl, pyridazin-di-yl, pyrimidin-di-yl, pyrazin-di-yl, furan-di-yl, or thiophen-di-yl rings;

X is independently at each occurrence a bond or C≡C;

$R^6$ is hydrogen, $C_1$–$C_{12}$ alkyl, $C_2$–$C_{12}$ alkynyl, $C_1$–$C_{12}$ alkoxy, $C_1$–$C_{12}$ alkylthio, halo, or —O—$(CH_2)_m$—[O—$(CH_2)_n]_p$—O—($C_1$–$C_{12}$ alkyl), or —O—$(CH_2)_q$—Z—$R^8$;

$R^7$ is independently at each occurrence hydrogen, hydroxy, amino, azido, $OR^5$, O—Pg, or $NH_p$—Pg;

$R^{7'}$ is $CHR^7CH_2R^7$, $CHR^7CH_2OR^9$, ethyl, $CHR^7CO_2H$, $CHR^7CH_2O$—Pg, or $CHR^7C(O)$—Pg;

$R^{7''}$ is hydrogen, $CH_2R^7$, $CH_2OR^9$, methyl, $CO_2H$, $CH_2O$—Pg, $CH_2NH_p$—Pg, or $C(O)$—Pg;

m, n, and q are independently 2, 3 or 4;

p is 0 or 1;

Z is pyrrolidin-di-yl, piperidin-di-yl, or piperazin-di-yl;

$R^8$ is hydrogen, $C_1$–$C_{12}$ alkyl, benzyl, or methyl($C_3$–$C_{12}$ cycloalkyl);

$R^9$ is $SO_3H$ or a moiety of the formula:

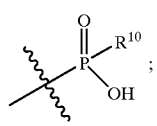

$R^{10}$ is hydroxy, $C_1$–$C_6$ alkyl, $C_1$–$C_6$ alkoxy, phenyl, phenoxy, p-halophenyl, p-halophenoxy, p-nitrophenyl, p-nitrophenoxy, benzyl, benzyloxy, p-halobenzyl, p-halobenzyloxy, p-nitrobenzyl, or p-nitrobenzyloxy; and Pg is a hydroxy, amino, amido or carboxy protecting group; with the proviso that the total number of $R^7$ substituents that are $OR^5$ groups does not exceed two; or a pharmaceutical salt or solvate thereof, which are useful as antifungal and antiparasitic agents or intermediates to such agents.

Furthermore, the present invention relates to pharmaceutical formulations comprising one or more pharmaceutical carriers, diluents or excipients and a compound of formula I.

Moreover, the present invention relates to methods for inhibiting fungal and parasitic activity comprising administering an effective amount of a compound of formula I to a host in need of such treatment.

DETAILED DESCRIPTION OF THE INVENTION

Definitions

The Compounds:

As used herein, the term "$C_1$–$C_{12}$ alkyl" refers to a straight or branched saturated alkyl chain having from one to twelve carbon atoms. Typical $C_1$–$C_{12}$ alkyl groups include methyl, ethyl, propyl, isopropyl, butyl, sec-butyl, t-butyl, pentyl, 5-methylpentyl, hexyl, heptyl, 3,3-dimethylheptyl, octyl, 2-methyl-octyl, nonyl, decyl, undecyl, dodecyl and the like. The term "$C_1$–$C_{12}$ alkyl" includes within its definition the terms "$C_1$–$C_6$ alkyl", "$C_1$–$C_4$ alkyl", and "$C_3$–$C_{12}$ cycloalkyl". The term "$C_3$–$C_{12}$ cycloalkyl" refers to a cyclic saturated alkyl chain having from 3 to 12 carbon atoms. Moreover, the term "$C_3$–$C_{12}$ cycloalkyl" includes within its definition the term "$C_3$–$C_7$ cycloalkyl".

The term "$C_2$–$C_{12}$ alkynyl" refers to a straight or branched mono-alkynyl chain having from two to twelve carbon atoms. Typical $C_2$–$C_{12}$ alkynyl groups include ethynyl, 1-propyn-1-yl, 1-propyn-2-yl, 1-butyn-1-yl, 1-butyn-3-yl, 1-pentyn-3-yl, 4-pentyn-2-yl, 1-hexyn-3-yl, 3-hexyn-1-yl, 5-methyl-3-hexyn-1-yl, 5-octyn-1-yl, 7-octyn-1-yl, 4-decyn-1-yl, 6-decyn-1-yl and the like.

The term "halo" refers to chloro, fluoro, bromo or iodo.

The term "$C_1$–$C_{12}$ alkoxy" refers to a $C_1$–$C_{12}$ alkyl group attached through an oxygen atom. Typical $C_1$–$C_{12}$ alkoxy groups include methoxy, ethoxy, propoxy, butoxy, sec-butoxy, n-pentoxy, 5-methyl-hexoxy, heptoxy, octyloxy, decyloxy dodecyloxy and the like. The term "$C_1$–$C_{12}$ alkoxy" includes within its definition the terms "$C_1$–$C_6$ alkoxy", "$C_3$–$C_7$ alkoxy", and "$C_1$–$C_4$ alkoxy".

The term "$C_1$–$C_{12}$ alkylthio" refers to a $C_1$–$C_{12}$ alkyl group attached through a sulfur atom. Typical $C_1$–$C_{12}$ alkylthio groups include methylthio, ethylthio, propylthio, isopropylthio, butylthio, 3-methyl-heptylthio, octylthio, 5,5-dimethyl-hexylthio and the like. The term "$C_1$–$C_{12}$ alkylthio" includes within its definition the terms "$C_1$–$C_6$ alkylthio" and "$C_1$–$C_4$ alkylthio".

The symbol "O—Pg" and term "hydroxy protecting group" refer to a substituent of a hydroxy group that is commonly employed to block or protect the hydroxy functionality while reactions are carried out on other functional groups on the compound. This substituent, when taken with the oxygen to which it is attached, may form an ether, e.g., methyl, methoxymethyl, and benzyloxymethyl ether, a silyl ether, an ester, e.g. acetoxy, or a sulfonate moiety, e.g. methane and p-toluenesulfonate. The exact genus and species of hydroxy protecting group is not critical so long as the derivatized hydroxy group is stable to the conditions of subsequent reaction(s) and can be removed at the appropriate point without disrupting the remainder of the molecule. A preferred hydroxy protecting group is acetyl. Specific examples of hydroxy protecting groups are described in T. W. Greene, "Protective Groups in Organic Synthesis," John Wiley and Sons, New York, N.Y., (2nd ed., 1991), (hereafter referred to as Greene) chapters 2 and 3 and in the Preparations and Examples section which follows.

The symbol "$NH_P$—Pg" and term "amino protecting group" as used in the specification refer to a substituent of the amino group commonly employed to block or protect the amino functionality while reacting other functional groups on the compound. When p is 0, the amino protecting group, when taken with the nitrogen to which it is attached, forms a cyclic imide, e.g., phthalimido and tetrachlorophthalimido. When p is 1, the protecting group, when taken with the nitrogen to which it is attached, can form a carbamate, e.g., methyl, ethyl, and 9-fluorenylmethylcarbamate; or an amide, e.g., N-formyl and N-acetylamide. The exact genus and species of amino protecting group employed is not critical so long as the derivatized amino group is stable to the condition of subsequent reaction(s) on other positions of the intermediate molecule and can be selectively removed at the appropriate point without disrupting the remainder of the molecule including any other amino protecting group(s). Preferred amino protecting groups are t-butoxycarbonyl (t-Boc), allyloxycarbonyl, phthalimido, and benzyloxycarbonyl (CbZ). Further examples of groups referred to by the above terms are described in *Greene* at chapter 7.

The symbol C(O)—Pg and the term "carboxy protecting group" refer to a substituent of a carbonyl that is commonly employed to block or protect the carboxy functionality while reactions are carried out on other functional groups on the compound. This substituent, when taken with the carbonyl to which it is attached, may form an ester, e.g., $C_1$–$C_6$ alkyl, substituted $C_1$–$C_6$ alkyl, $C_2$–$C_6$ alkenyl, substituted $C_2$–$C_6$ alkenyl, benzyl, substituted benzyl, benzhydryl, substituted benzhydryl, trityl, substituted trityl, and trialkylsilyl ester. The exact species of carboxy protecting group is not critical so long as the derivatized carboxy group is stable to the conditions of subsequent reaction(s) and can be removed at the appropriate point without disrupting the remainder of the molecule. Other examples of groups referred to by the above terms are described in Greene, at chapter 5.

The symbol "C(O)NH—Pg" and term "amido protecting group" as used in the specification refer to a substituent of an amide commonly employed to block or protect the amino portion while reacting other functional groups on the compound. This protecting group, when taken with the nitrogen to which it is attached, may form an amide, e.g. N-allyl, N-methoxymethyl, and N-benzyloxymethyl amide. The exact species of amido protecting group employed is not critical so long as the derivatized amido group is stable to the condition of subsequent reaction(s) on other positions of the intermediate molecule and can be selectively removed at the appropriate point without disrupting the remainder of the molecule including any other amido protecting group(s). Other examples of groups referred to by the above terms are described in *Greene,* at chapter 7, pg. 397.

The term "pharmaceutical salt" as used herein, refers to salts of the compounds of formula I which, at the doses administered, are substantially non-toxic to living organisms. Typical pharmaceutical salts include those prepared by reaction of the compounds of the present invention with a mineral or organic acid or inorganic base. Such salts are known as acid addition and base addition salts. For further exemplification of pharmaceutical salts, see e.g. Berge, S. M, Bighley, L. D., and Monkhouse, D.C., *J. Pharm. Sci.,* 66, 1, 1977.

The term "solvate" represents an aggregate that comprises one or more molecules of the solute, such as a formula I compound, with one or more molecules of solvent.

Reagents:

The term "suitable solvent" refers to any solvent, or mixture of solvents, inert to the ongoing reaction that sufficiently solubilizes the reactants to afford a medium within which to effect the desired reaction.

The term "thermodynamic base" refers to a base which provides a reversible deprotonation of an acidic substrate or is a proton trap for those protons that may be produced as byproducts of a given reaction, and is reactive enough to effect the desired reaction without significantly effecting any undesired reactions. Examples of thermodynamic bases include, but are not limited to, acetates, acetate dihydrates, carbonates, bicarbonates, $C_1$–$C_4$ alkoxides, and hydroxides (e.g. lithium, sodium, or potassium acetate, acetate dihydrate, carbonate, bicarbonate, methoxide, or hydroxide), tri-($C_1$–$C_4$ alkyl)amines, or aromatic nitrogen containing heterocycles (e.g. imidazole and pyridine).

The Methods:

The term "inhibiting" includes prohibiting, stopping, retarding, alleviating, ameliorating, halting, restraining, slowing or reversing the progression, or reducing the severity of the growth or any attending characteristics, symptoms, and results from the existence of a parasite or fungus. As such, these methods include both medical therapeutic (acute) and/or prophylactic (prevention) administration as appropriate.

The term "effective amount," means an amount of a compound of formula I which is capable of inhibiting fungal and/or parasitic activity.

Preferred Embodiments

Compounds:

Preferred compounds of this invention are those compounds of formula I where:

R is hydroxy at each occurrence;

$R^1$, $R^2$, and $R^3$ are each methyl; and $R^4$ is a moiety of the formula:

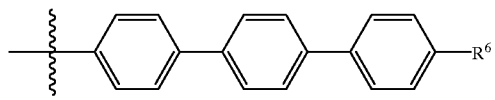

or

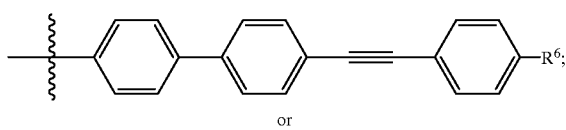

or

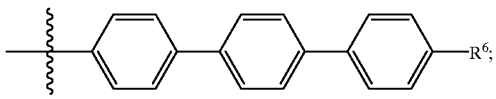

a pharmaceutical salt or solvate thereof.

Of these compounds, more preferred are those compounds of formula I where:

$R^4$ is a moiety of the formula:

$R^5$ is a moiety of the formula:

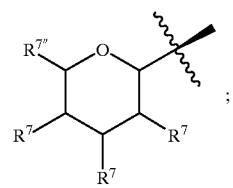

$R^6$ is hydrogen or $C_3$–$C_7$ alkoxy;

$R^7$ is independently at each occurrence hydrogen, hydroxy, amino, or $OR^5$; and $R^{7"}$ is hydrogen, $CH_2R^7$, $CH_2OR^9$, methyl, $CO_2H$, or C(O)—Pg; or a pharmaceutical salt or solvate thereof.

Of these compounds, further preferred are those compounds of formula I where:

$R^6$ is n-pentoxy;

$R^7$ is independently at each occurrence hydroxy or amino;

$R^{7"}$ is hydrogen, hydroxymethyl, $CH_2OR^9$, methyl, or $CO_2Me$; and $R^9$ is a moiety of the formula:

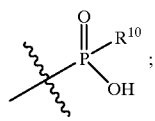

or a pharmaceutical salt thereof.

Of these compounds even more preferred are those compounds of formula 1 where:

$R^7$ is independently at each occurrence hydroxy;

$R^{10}$ is $C_1$–$C_4$ alkyl; or a pharmaceutical salt thereof.

Preferred pharmaceutical acid addition salts are those formed with mineral acids such as hydrochloric acid and sulfuric acid, and those formed with organic acids such as maleic acid, tartaric acid, and methanesulfonic acid.

Preferred pharmaceutical base addition salts are the potassium and sodium salt forms.

Methods:

Preferred methods include inhibiting fungal activity arising from *Candida albicans*, *Aspergillus fumigatis*, and *Candida parapsilosis* and inhibiting parasitic activity arising from *Pneumocystis carinii*.

Synthesis

The compounds of formula I may be prepared from compounds of formula II(d) as illustrated in Scheme 1 below where R, $R^1$, $R^2$, $R^3$, $R^4$, and $R^5$ are as defined above.

Scheme 1
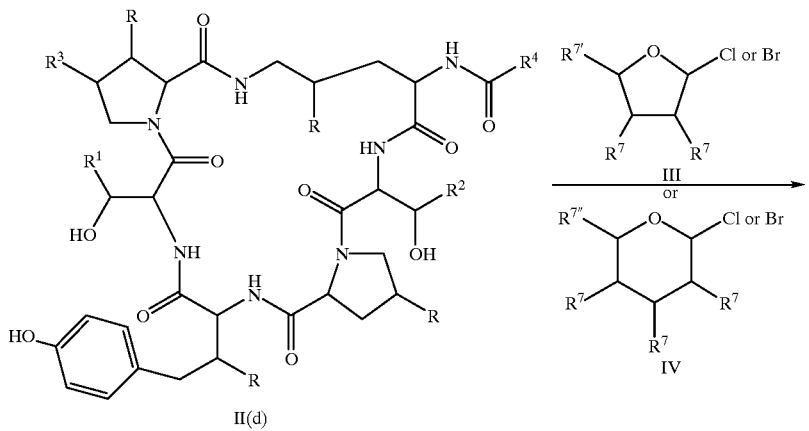
II(d)
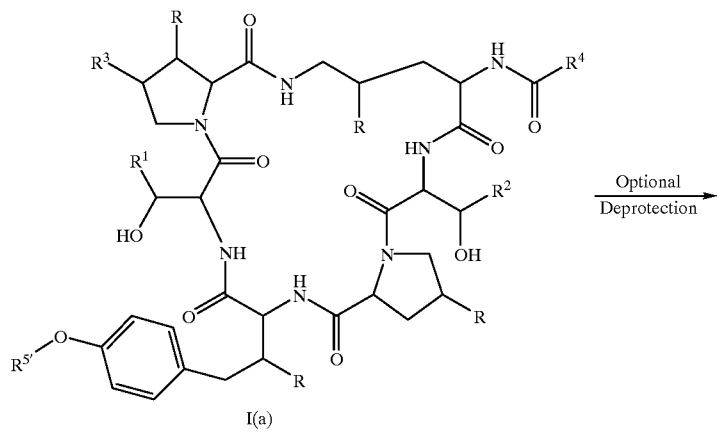
I(a)
Optional Deprotection
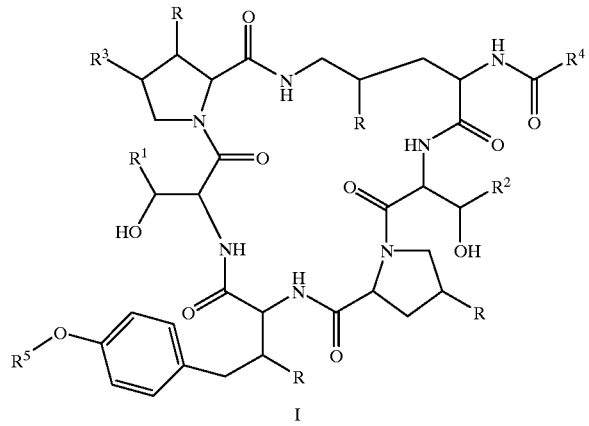
I

A compound of formula II(d) may be O-glycosylated by procedures known in the art to form a compound of formula I(a). See e.g., Toshima, K., and Tatsuta, K., "Recent Progress in O-Glycosylation Methods and Its Application to Natural Products Synthesis," *Chem. Rev.*, 93:1503, 1993. For example, a protected mono, di, or trisaccharide of formula III or IV may be added to a compound of formula II(d), dissolved or suspended in a suitable solvent, in the presence of a suitable thermodynamic base and suitable activating reagent. Such a procedure is a well known variant of the "Koenigs and Knorr Reaction". Id. A convenient and preferred solvent for this procedure is an aprotic solvent such as tetrahydrofuran. A convenient and preferred thermodynamic base is silver carbonate. Suitable activating reagents include, but are not limited to, silver trifluoromethanesulfonate, silver(I) oxide, silver carbonate, silver perchlorate, silver nitrate, silver silicate, mercury(II) cyanide, bromide, chloride, and iodide, mixtures thereof, and the like. A convenient and preferred activating reagent is silver trifluoromethanesulfonate. See Example 1 below for further instruction on reaction conditions.

The compounds of formula I, where any of $R^7$, $R^{7'}$, or $R^{7''}$ are amino may be formed from the compounds of formula I where $R^7$, $R^{7'}$, or $R^{7''}$ are azido as described in Example 41 below or by analogous procedures well known in the art. See, e.g., Larock, "Comprehensive Organic Transformations," pg. 409, VCH Publishers, New York, N.Y., 1989.

The compounds of formula I where $R^{7'}$ or $R^{7''}$ is $CHR^7CH_2OH$ or hydroxymethyl respectively may be phosphorylated or phosphonylated by reaction with an appropriately substituted dichloro-phosphate or phosphonic acid of formula V:

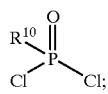

V in the presence of a suitable base to provide, following an aqueous workup, a compound of formula I where $R^9$ is a moiety of the formula:

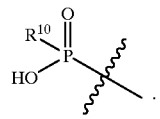

Suitable bases include lithium trimethylsilanolate (LiOTMS), and lithium bis(trimethylsilyl)amide (LHMDS). A convenient and preferred solvent is an aprotic solvent such as tetrahydrofuran and/or dimethylformamide.

Alternatively, the compounds of formula I where $R^{7'}$ or $R^{7''}$ is $CHR^7CH_2OH$ or hydroxymethyl respectively may be sulfated by reaction with a suitable sulfation reagent by the procedures taught in Guiseley and Ruoff, *J. Org. Chem.*, 26:1248, 1961.

The protected compound of formula I(a) may optionally have its protecting group(s) removed to form a compound of formula I. Initial choices of protecting groups, and methods for their removal, are well known in the art. See, e.g., *Greene* cited above. Preferred choices and methods may be found in the Examples section which follows, e.g., Example 40.

The pharmaceutical salts of the invention are typically formed by reacting a compound of formula I(a) or I with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as methylene chloride for base addition salts. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like.

It should be recognized that the particular counterion forming a part of any salt of this invention is not of a critical nature, so long as the salt as a whole is pharmacologically acceptable and as long as the counterion does not contribute undesired qualities to the salt as a whole.

Compounds of formula I(d) may be prepared as illustrated in Scheme 2 below where $R^{nat}$ is a side chain found on a naturally occurring cyclic peptide described above, $R^{11}$ and $R^{11'}$ are independently hydrogen or hydroxy, and R, $R^1$, $R^2$, $R^3$, $R^4$, and $R^5$ are as defined above Scheme 2

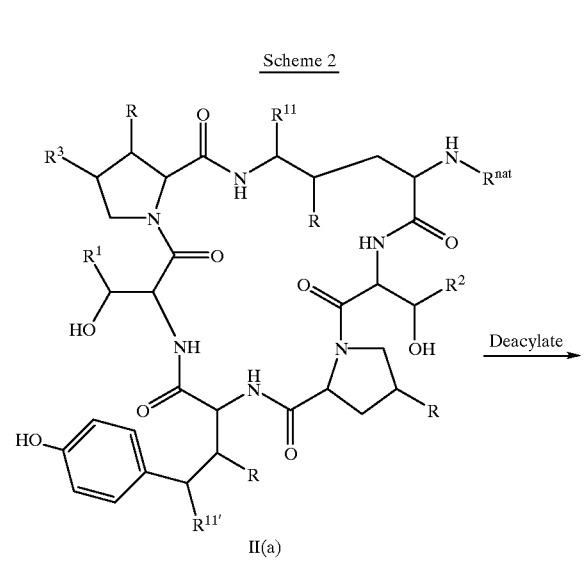

II(a)

Deacylate

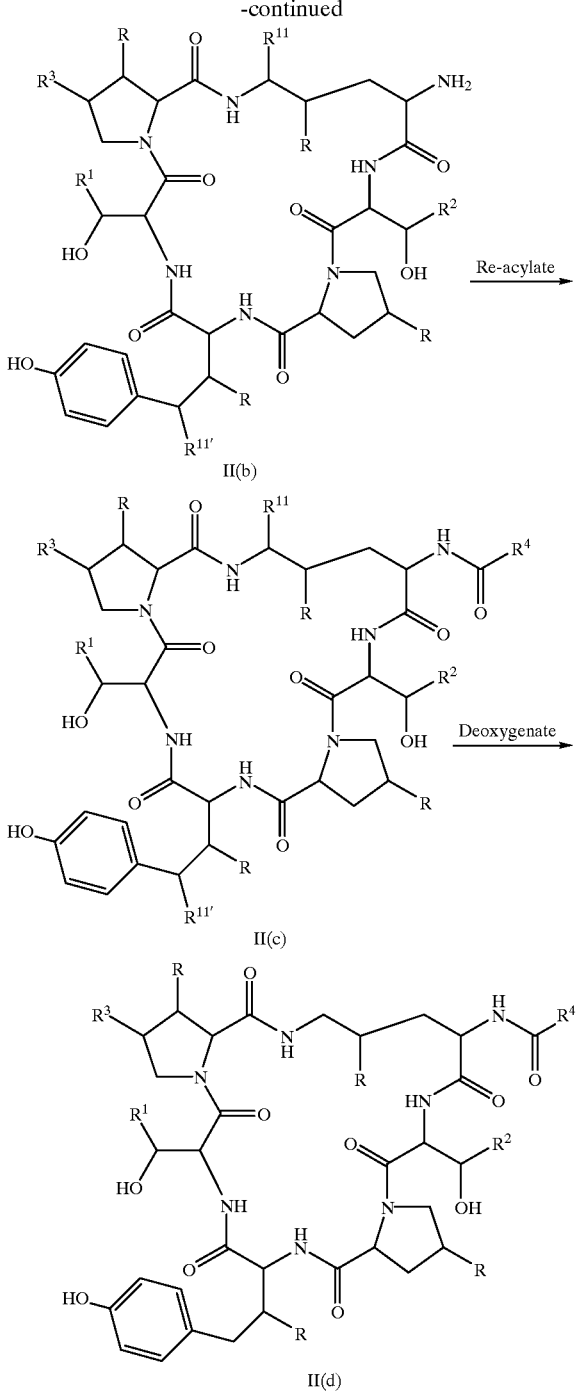

A naturally occurring cyclic peptide of formula II(a) may be deacylated using procedures known in the art to provide an amino nucleus of formula II(b). This reaction is typically carried out enzymatically by exposing the naturally occurring cyclic peptide to a deacylase enzyme. The deacylase enzyme may be obtained from the microorganism *Actinoplanes utahensis* and used substantially as described in U.S. Pat. Nos. 4,293,482 and 4,304,716, the teachings of each are herein incorporated by reference. The deacylase enzyme may also be obtained from the Pseudomonas species. Deacylation may be accomplished using whole cells of *Actinoplanes utahensis* or Pseudomonas or the crude or purified enzyme thereof or using an immobilized form of the enzyme. See European Patent Application No. 0 460 882 (Dec. 11, 1991). Examples of naturally occurring cyclic peptides which may be used as starting materials include aculeacin (palmitoyl side chain), tetrahydroechinocandin B (stearoyl side chain), mulundocandin (branched $C_{15}$ side chain), L-671,329 ($C_{16}$ branched side chain), S 31794/F1 (tetradecanoyl side chain), sporiofungin ($C_{15}$ branched side chain), FR901379 (palmitoyl side chain) and the like. A preferred naturally occurring cyclic peptide is echinocandin B (a compound of formula II(a) where $R^1$, $R^2$ and $R^3$ are each methyl, R, $R^{11'}$, and $R^{11'}$ are hydroxy at each occurrence, and $R^{nat}$ is linoleoyl).

The amino nucleus of formula II(b) may be re-acylated, and the hydroxy groups when present at $R^{11}$ and/or $R^{11'}$ removed (deoxygenated), by procedures taught in U.S. Pat. Nos. 5,646,111, and 5,693,611, the teachings of each are herein incorporated by reference, to provide the compounds of formula II(d). See Preparation 11 and 12 below for an example of these two transformations.

The cyclic peptides of formula II(a) may be prepared by fermentation of known microorganisms. For example, the cyclic peptide of formula II(a) where $R^1$, $R^2$ and $R^3$ are methyl, R, $R^{11}$, and $R^{11'}$ are hydroxy at each occurrence (cyclic nucleus corresponding to A-30912A) may be prepared using the procedure detailed in Abbott, et al., U.S. Pat. No. 4,293,482, the teachings of which are herein incorporated by reference. The cyclic peptide of formula II(a) where $R^1$, $R^2$ and $R^3$ are methyl, $R^{11}$ is hydroxy, $R^{11'}$ is hydrogen, and R is hydroxy at each occurrence (cyclic nucleus corresponding to A-30912B) may be prepared using the procedure detailed in Abbott, et al., U.S. Pat. No. 4,299,763, the teachings of which are herein incorporated by reference. Aculeacin may be prepared using the procedure detailed in Mizuno, et al., U.S. Pat. No. 3,978,210, the teachings of which are herein incorporated by reference. The cyclic peptide of formula II(a) where $R^1$ is $CH_2C(O)NH_2$, $R^2$ is methyl, $R^3$ is hydrogen, and R, $R^{11}$, and $R^{11'}$ are hydroxy at each occurrence may be prepared by deacylating the cyclic peptide prepared using the procedure detailed in Chen, et al., U.S. Pat. No. 5,198,421, the teachings of which are herein incorporated by reference. Furthermore, cyclic peptides of formula II(d) where $R^4$ contains 1 or more heterocyclic rings may be prepared as taught in U.S. Pat. No. 5,693,611, the teachings of which are herein incorporated by reference.

Compounds of formula III, IV, and V are known in the art and to the extent not commercially available may be synthesized by techniques well known in the synthetic chemical arts. See, e.g., the previously incorporated by reference U.S. Pat. Nos. 5,646,111 and 5,693,611 for preparation of the acyl groups at $R^4$. See also, Collins and Ferrier, "Monosaccharides: Their Chemistry and Their Roles in Natural Products," John Wiley and Sons, New York, N.Y., 1995, and "Methods in Carbohydrate Chemistry", Vol VI, Academic Press, New York, N.Y., 1980 for instruction on preparing compounds of formula III and IV.

For example, compounds of formula IV, and by analogy compounds of formula III, may be prepared as illustrated in Scheme 3 below where $R^7$, $R^{7'}$, and $R^{7''}$ are as described above.

Scheme 3

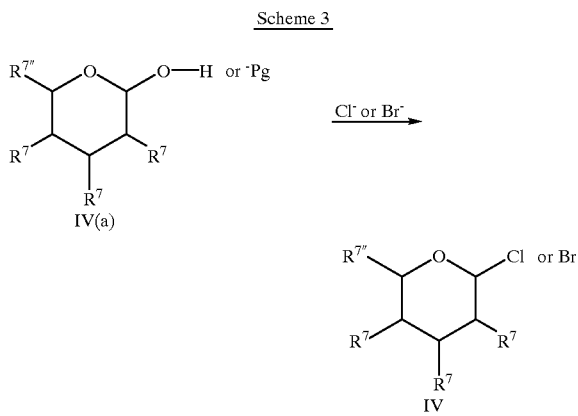

Compounds of formula IV(a), dissolved or suspended in a suitable solvent, may be treated with a source of chloride or bromide ion, to provide the compounds of formula IV. Suitable sources of ion include acetyl chloride, hydrochloric acid, hydrobromic acid, mixtures thereof, and the like. A preferred solvent is the source of ion i.e. a preferred method of performing the reaction is to run it neat. For further instruction on this transformation, see Preparations 8 and 9 below.

Compounds of formula IV(a) where $R^7$ is hydroxy at each occurrence and $R^{7"}$ is either hydrogen or hydroxymethyl are known as carbohydrates or monosaccharides (sugars). These sugars can be modified by replacing one or more hydroxy groups with hydrogen, azide, or amino to provide the rest of the compounds of formula IV(a). Such compounds may be prepared as illustrated in Scheme 4 below where Lg is an activated hydroxy leaving group. Positions left open for substitution in Scheme 4 are assumed to be hydrogen, azide, protected hydroxy, or protected amino.

Scheme 4

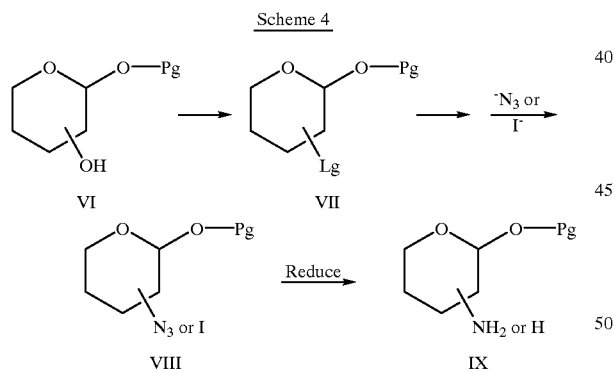

A commercially available compound of formula VI may have its hydroxy group(s) activated for nucleophilic displacement by standard techniques known in the art. For example, the hydroxy group can be sulfonylated with methane-benzene-, or p-toluene-sulfonyl chloride (or bromide) to provide a compound of formula VII where Lg is $OSO_2Me$, $OSO_2$-phenyl, or $OSO_2$-p-toluenyl. An example of this transformation is illustrated in Preparation 1 below. At this point, the leaving group can be displaced by azide ion, e.g., from sodium or potassium azide as in Preparation 2. Alternatively, the leaving group can be displaced by iodide ion from, e.g., sodium or potassium iodide as in Preparation 3. The resulting compound of formula VIII may be reduced to form a compound of formula IX where one or more of $R^7$, $R^{7'}$, or $R^{7"}$ is amino or hydrogen by catalytic hydrogenation or with a reducing agent such as nickel chloride hexahydrate as described in Preparation 4 and Example 41 below. It is preferred that when an amino group is desired in the final product compound of formula I, that any azido groups be converted to amino groups after coupling to the compound of formula II(a).

The optimal time for performing the reactions of Schemes 1–4 can be determined by monitoring the progress of the reaction by conventional chromatographic techniques. Choice of reaction solvent is generally not critical so long as the solvent employed is inert to the ongoing reaction and sufficiently solubilizes the reactants to afford a medium within which to effect the desired reaction. Unless otherwise indicated, all of the reactions described herein are preferably conducted under an inert atmosphere. A preferred inert atmosphere is nitrogen. Once a reaction is complete, the intermediate compound may be isolated by procedures well-known in the art, for example, the compound may be crystallized or precipitated and then collected by filtration, or the reaction solvent may be removed by extraction, evaporation or decantation. The intermediate compound may be further purified, if desired, by common techniques such as crystallization, precipitation, or chromatography over solid supports such as silica gel, alumina and the like, before carrying out the next step of the reaction scheme.

The following Preparations and Examples further describe how to synthesize the compounds of the present invention. The terms high resolution fast atom bombardment mass spectroscopy, fast atom bombardment mass spectroscopy, high performance liquid chromatography, and thin layer chromatography are abbreviated "HRMS(FAB)", "MS(FAB)", "HPLC" and "TLC", respectively.

EXAMPLES

Preparations

Preparation 1

1,2,3,4-Tetra-O-Acetyl-6-Deoxy-6-Methanesulfonyl-β-D-Glucopyranose

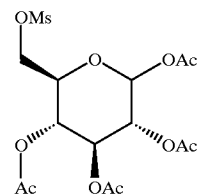

In a 100 mL round bottom flask containing 50 mL dichloromethane at 0° C. was placed 1,2,3,4-tetra-O-acetyl-β-D-glucopyranose (4.62 g, 13.26 mmol). To this solution was added triethylamine (2.77 mL, 19.90 mmol) followed by dropwise addition of methanesulfonyl chloride (1.23 mL, 15.9 mmol). The reaction was then warmed to room temperature and stirred for 3 hours at which time the reaction was diluted with 100 mL dichloromethane. The organic layer was then washed two times each with 50 mL of water, 1N aqueous hydrochloric acid, saturated aqueous sodium bicarbonate and brine. The organic layer was dried over magnesium sulfate, filtered and the solvent removed in vacuo to yield 4.45 g of crude title compound as a white solid which was used directly in Preparation 2. (79%).

Preparation 2

1,2,3,4-Tetra-O-Acetyl-6-Azido-6-Deoxy-β-D-Glucopyranose

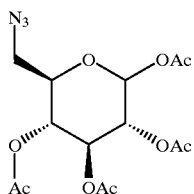

A 100 mL round bottom flask was charged with 40 mL anhydrous dimethylformamide, sodium azide (2.19 g, 33.6 mmol), and crude 1,2,3,4-tetra-O-acetyl-6-deoxy-6-methanesulfonyl-β-D-glucopyranose (1.9374 g, 4.54 mmol). The resulting homogeneous solution was heated to 70° C. and allowed to react for 10 hours. The reaction was then diluted with 200 mL of ethyl acetate and washed with copious amounts of water. The organic layer was dried over magnesium sulfate, filtered and the solvent removed in vacuo. The resulting brown solid was purified by column chromatography over silica gel to yield 668.3 mg of the title compound (39.5%). MS (FAB) calculated for $C_{14}H_{19}N_3O_9$ (M—OCOCH$_3$) 314.1, found 314.1.

Preparation 3

1,2,3,4-Tetra-O-Acetyl-6-Deoxy-6-Iodo-β-D-glucopyranose

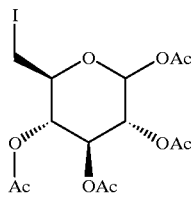

A 1 L round bottom flask containing 500 mL of methyl ethyl ketone was charged with 1,2,3,4-tetra-O-acetyl-6-deoxy-6-methanesulfonyl-β-D-glucopyranose (4.45 g, 10.44 mmol) and sodium iodide (15.73 g, 104.9 mmol). The reaction was heated at reflux for 24 hours. The solvent was removed in vacuo and the resulting residue was taken up in 250 mL dichloromethane. The organic layer was washed with sodium thiosulfate (2×100 mL), water (2×100 mL) and once with 100 mL of brine. The organic layer was dried over magnesium sulfate, filtered and the solvent removed in vacuo to yield crude 1,2,3,4-tetra-O-acetyl-6-deoxy-6-iodo-β-D-glucopyranose as a white solid (4.99 g) which was used directly in Preparation 4.

Preparation 4

1,2,3,4-Tetra-O-Acetyl-6-Deoxy-β-D-Glucopyranose

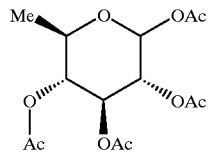

1,2,3,4-Tetra-O-acetyl-6-deoxy-6-iodo-β-D-glucopyranose (251.6 mg, 0.549 mmol) was dissolved in 20 mL of ethanol. To this solution was added 1 mL of triethylamine and 5% palladium on carbon (50.0 mg). The reaction mixture was exposed to 60 psi of hydrogen in a Parr apparatus at room temperature for 5 hours. The palladium on carbon was filtered off and the ethanol was removed in vacuo to yield a white solid. Purification via column chromatography over silica gel yielded 82.3 mg of the title compound as a white solid. (45w). MS(FAB) calculated for $C_{14}H_{20}O_9$ (M+): 332.1. Found: 331.1.

Preparation 5

1,2,5,6-Diacetone-4-p-Toluenesulfonyl-D-Allofuranose

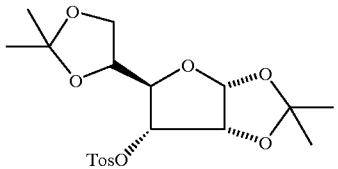

A 500 mL round bottom flask containing 160 mL of pyridine was charged with 1,2,5,6-diacetone-D-allofuranose (40.72 g, 156.44 mmol) and p-toluenesulfonyl chloride (45.67 g, 239.53 mmol). The reaction was allowed to stir at room temperature for 27 hours. The reaction mixture was poured into 1.5 L of ice water and, upon melting, was filtered and dried in a vacuum oven at 30° C. to yield 56.74 g of the title compound which was used crude in Preparation 6.

Preparation 6

1,2,5,6-Diacetone-4-p-Azido-D-Allofuranose

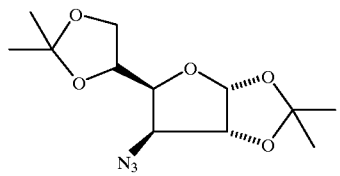

In a 2 L round bottom flask containing 1 L of dimethylformamide was added 1,2,5,6-diacetone-4-p-toluenesulfonyl-D-allofuranose (56.44 g, 136.17 mmol) and sodium azide (142.12 g, 2.186 mol). The reaction mixture was heated to reflux and allowed to react for 20 hours. The reaction was cooled to room temperature and the dimethylformamide was removed in vacuo. The resulting residue was partitioned between 250 mL ethyl acetate and 250 mL water.

The organic layer was washed with 300 of water and brine. The organic layer was dried over magnesium sulfate, filtered and the solvent removed in vauco to obtain a crude brown oil. Purification via column chromatography over silica gel (10% ethyl acetate/hexanes) yielded the title compound.

Preparation 7

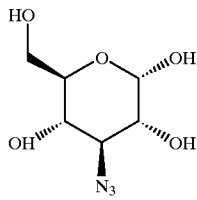

1,2,5,6-Diacetone-4-p-azido-D-allofuranose was suspended in 50 mL of water in a 500 mL round bottom flask. To this suspension was added Dowex 50 X 8–100 acidic resin (20 g) and the reaction mixture was heated at 60° C. for 16 hours. The resin was then filtered and the filtrate was lyophilized to yield 9.92 g of the title compound as a white solid.

Preparation 8

α-D-Acetochlororhamnose

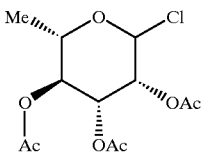

In a 25 mL round bottom flask containing 10 mL of acetyl chloride was placed 1.0117 g of L-rhamnose. The reaction was stirred for 48 h at room temperature. The reaction was diluted with 100 mL of dichloromethane and washed with 50 mL ice water and then 50 mL of cold saturated aqueous sodium bicarbonate. The organic layer was dried over magnesium sulfate and filtered. The solvent was removed in vacuo and the product used without further purification as in Example 1.

The following compounds were prepared by the procedure of Preparation 8 and used directly as in Example 1:

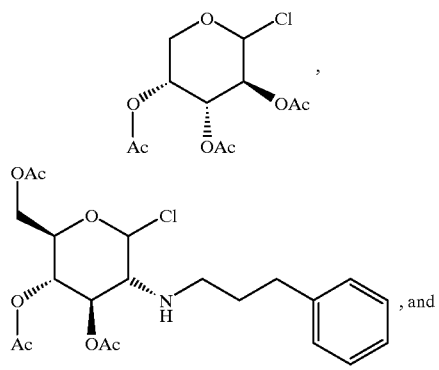

-continued

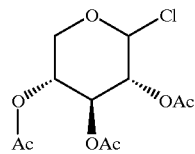

Preparation 9

2,3,4-Tri-O-Acetyl-6-Deoxy-α-D-Glucopyranosyl Bromide:

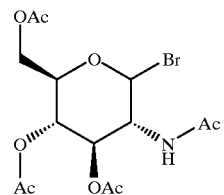

In a 10 mL round bottom flask containing 10 mL of glacial acetic acid was placed 6-deoxyglucose (332.3 mg) and the reaction was cooled to 0° C. Hydrobromic acid in glacial acetic acid (5 mL of a 30 wt. % solution) was added dropwise. The reaction was stirred for 4 hours. The reaction was diluted with 100 mL of dichloromethane and washed with 50 mL ice water and then 50 mL of cold saturated aqueous sodium bicarbonate. The organic layer was dried over magnesium sulfate and filtered. The solvent was removed in vacuo to yield the title compound as a yellow solid (636.5 mg, 85.4%) and the product was used without further purification as in Example 1. MS (FAB) calculated for $C_{12}H_{17}O_7Br$ (M−Br) 273.1, found 273.1.

The following compounds were prepared by the procedure of Preparation 9 and used directly as in Example 1:

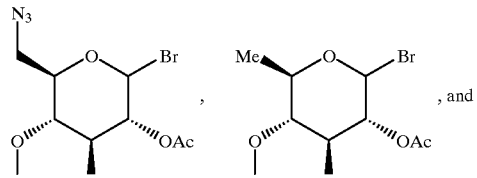

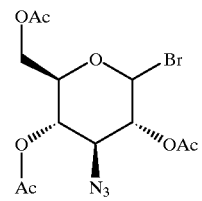

Preparation 10

3,4,6-Tri-O-Acetyl-2-Azido-2-Deoxy-α-D-Glucopyranosyl Bromide

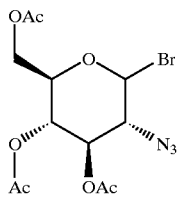

A 1 L flask containing 400 mL of acetonitrile was charged with sodium azide (7.75 g, 119.2 mmol) and ceric ammonium nitrate (120.7 g, 219.4 mmol). The resulting suspension was cooled to −30° C. and a solution of tri-O-acetyl-D-glucal (20.75 g, 76.22 mmol) in 100 mL acetonitrile was added to it dropwise. The reaction mixture was stirred at −30° C. for 20 hours and then warmed to room temperature, taken up in 800 mL of diethyl ether and washed with water (3×250 mL). The organics were dried over magnesium sulfate, filtered, and the solvent removed in vacuo to yield an oil. This oil was placed in a 1 L flask containing 400 mL of acetonitrile and lithium bromide (33.53 g, 386.1 mmol) and stirred at room temperature for at least 4 hours. The solvent was removed in vacuo and the resulting residue was taken up in 400 mL of dichloromethane. The organic layer was washed with water (2×250 mL), dried over magnesium sulfate and filtered. The solvent was removed in vacuo to yield the title compound as a gold oil which was used directly as in Example 1.

The following compounds were prepared by the procedure of Preparation 10 and used directly as in Example 1:

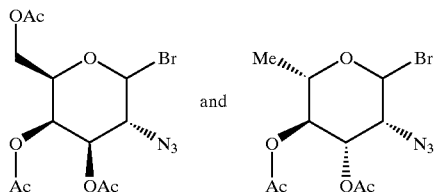

Preparation 11

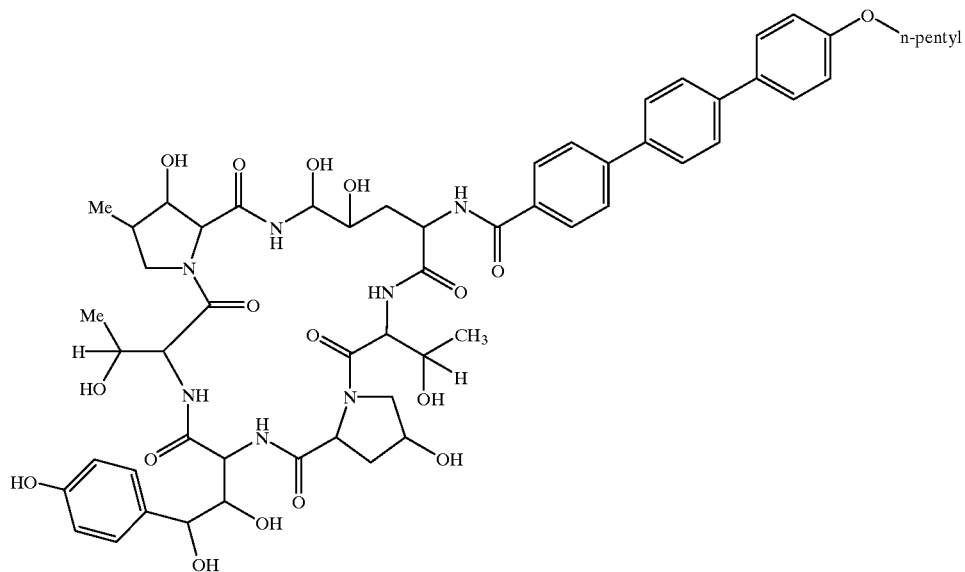

The A-30912A nucleus (348.1 g, 60.2 mmol) and the 2,4,5-trichlorophenol ester of [[(4"-pentyloxy)-1,1':4',1"-terphenyl]-4-carboxylic acid (26.0 g, 48.2 mmol) were combined in 8.5 L of dimethylformamide. The resultant reaction mixture was stirred for approximately 48 hours at room temperature and then the solvent was removed in vacuo to provide a residue. This residue was slurried in ether, collected by filtration, washed with methylene chloride and then dissolved in methanol or a 1:1 (v/v) acetonitrile/water mixture. The resultant solution is subjected to reverse phase HPLC (C18; eluent of 20–40% aqueous acetonitrile containing 0.5% monobasic ammonium phosphate (w/v); 20 mL/min.; 230 nm). After removing the unreacted A30912A nucleus, the desired product is eluted from the column using an eluent of aqueous acetonitrile. The fractions containing the desired product are combined and then concentrated in vacuo or lyophilized to provide 18 g of the title compound. MS (FAB): 1140.5103 ($M^{+1}$).

Preparation 12

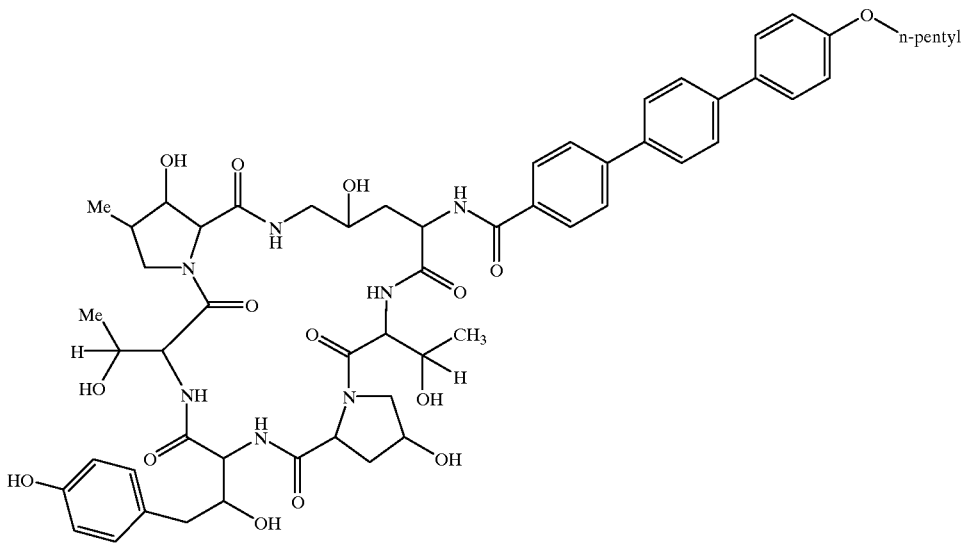

To a mixture of the compound of Preparation 11 (5 g, 4.4 mmol) and 17 mL of TFA in 250 mL of methylene chloride, was added 35 mL of triethylsilane. When the reaction was substantially complete, as indicated by HPLC (C18, eluent of 55% acetonitrile; 2 mL/min; 280 nm; $R_T$ (starting material)=4.19 min.; $R_T$ (product)=6.40 min.), the reaction mixture was concentrated in vacuo to provide a solid. This solid was slurried in 100 mL of 50% aqueous acetone and then dissolved by adjusting the pH of the mixture to approximately pH 7. The resultant solution was poured into a large volume of water (approximately 1 liter) resulting in the precipitation of a white solid. This solid was isolated by filtration through a sintered glass funnel, washed with diethyl ether and then dried in vacuo at 55° C. to provide 3.872 g of the title compound. (79%). MS(FAB): m/e 1108.7 (M+). HPLC: (eluent of 55% acetonitrile; 2 mL/min.; 280 nm): $R_T$=6.43 minutes.

Examples 1–43 have the following base structure:

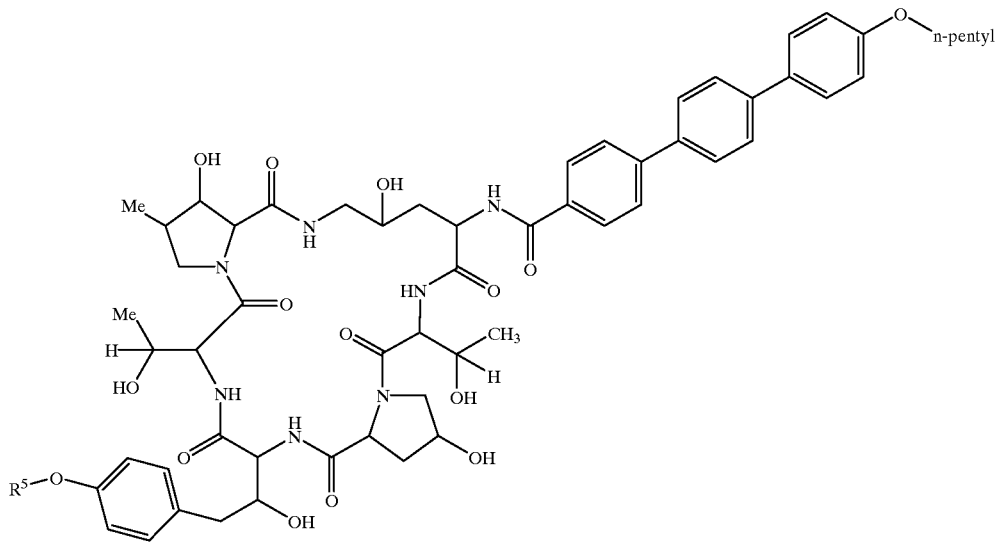

Example 1

$R^5 =$

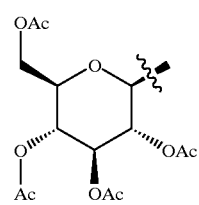

In a 100 mL round bottom flask containing 50 mL tetrahydrofuran and crushed 4 angstrom molecular sieves was placed the compound of Preparation 12 (3.0 g, 2.70 mmol) which was allowed to dissolve. To this solution was added silver carbonate (3.73 g, 13.5 mmol), acetobromoglucose (5.53 g, 13.4 mmol) and silver trifluoromethanesulfonate (3.83 g, 14.9 mmol) sequentially. The gray opaque reaction mixture was then allowed to stir overnight. The solvent was then removed in vacuo. The resulting gray solid was then taken up in methanol and filtered through a celite pad to remove the silver salts. The protected glycosylated product was then purified via reverse phase HPLC to yield 536.9 mg of a white solid. MS(FAB) calculated for $C_{72}H_{92}N_7O_{24}$(M+H): 1438.6. Found: 1438.7.

Examples 2–20, illustrated in Table 1, were prepared by the procedure of Example 1.

TABLE 1

| Ex.# | $R^5$ = | MS (FAB) calculated for | Found: |
|---|---|---|---|
| 2 | (structure: pyranose with OAc, OAc, OAc, OAc, OAc) | $C_{72}H_{91}N_7O_{24}$: 1438.6 | 1438.9 (M + H). |
| 3 | (structure: disaccharide with Ac—O, Ac—O, OAc, O—Ac, OAc, Ac, OAc, OAc) | $C_{84}H_{108}N_7O_{32}$: 1726.7. | 1748.8 (M + H). |
| 4 | (structure: pyranose with OAc, OAc, OAc, Ac, OAc) | $C_{72}H_{91}N_7O_{24}$: 1438.6. | 1438.8 (M + H). |
| 5 | (structure: Me−O, O=, O, OAc, Ac, OAc) | $C_{71}H_{89}N_7O_{24}$: 1424.534. | 1424.6 (M + H). |
| 6 | (structure: pyranose with OAc, O, NPth, Ac, OAc) | $C_{78}H_{92}N_8O_{24}$: 1525.6. | 1525.8 (M + H). |
| 7 | (structure: Me, O, O, OAc, Ac, OAc) | $C_{70}H_{89}N_7O_{22}$: 1380.5. | 1380.7 (M + H). |

TABLE 1-continued

| Ex.# | R⁵ = | MS (FAB) calculated for | Found: |
|---|---|---|---|
| 8 | (sugar with Me, OAc, OAc, OAc) | $C_{70}H_{89}N_7O_{22}$: 1380.5. | 1380.6 (M + H). |
| 9 | (sugar with Me, OAc, OAc, OAc) | $C_{70}H_{89}N_7O_{22}$: 1380.5. | 1380.7 (M + H). |
| 10 | (sugar with OAc, OAc, OAc, NHAc) | $C_{72}H_{92}N_8O_{23}$: 1437.6. | 1437.7 (M + H). |
| 11 | (sugar with OAc, OAc, OAc) | $C_{69}H_{87}N_7O_{22}$: 1366.5. | 1366.6 (M + H). |
| 12 | (sugar with OAc, OAc, OAc, NHCBz) | $C_{78}H_{96}N_8O_{24}$: 1529.7. | 1529.7 (M + H). |
| 13 | (sugar with Me, OAc, OAc, OAc) | $C_{70}H_{89}N_7O_{22}$: 1380.5. | 1380.7 (M + H). |
| 14 | (sugar with OAc, OAc, OAc, N₃) | $C_{70}H_{88}N_{10}O_{22}$: 1421.5. | 1421.7 (M + H). |
| 15 | (sugar with OAc, OAc, OAc, N₃) | $C_{70}H_{88}N_{10}O_{22}$: 1421.5. | 1421.8 (M + H). |

TABLE 1-continued

| Ex.# | R⁵ = | MS (FAB) calculated for | Found: |
|---|---|---|---|
| 16 | (sugar with Me, OAc, OAc, N₃) | $C_{68}H_{86}N_{10}O_{20}$: 1363.5. | 1363.5 (M + H). |
| 17 | (sugar with N₃, OAc, OAc, OAc) | $C_{70}H_{88}N_{10}O_{22}$: 1421.5. | 1460.6 (M + K). |
| 18 | (sugar with Me, OAc, OAc, OAc) | $C_{70}H_{89}N_{7}O_{22}$: 1380.5. | 1380.6 (M + H). |
| 19 | (sugar with OAc, OAc, OAc, N₃) | $C_{70}H_{88}N_{10}O_{22}$: 1421.5. | 1421.7 (M + H). |
| 20 | (sugar with OAc, OAc, OAc) | | |

Example 21

R⁵ = 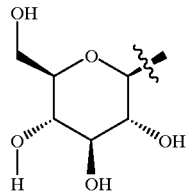

The compound of Example 1 (536.9 mg) was suspended in a mixture of 1:1 methanol/water (20 mL total). To this suspension was added potassium carbonate (250.5 mg, 1.812 mmol). Immediately after the addition the reaction became clear and was allowed to continue reacting for 30 minutes at room temperature. Reverse phase preparatory HPLC of the crude reaction mixture yielded 510.0 mg (14.8%) of the title compound after lyophilization. HRMS (FAB) calculated for $C_{64}H_{84}N_{7}O_{20}$ (M+H): 1270.5776. Found: 1270.5771.

Examples 22–39, illustrated in Table 2, were prepared by the procedure of Example 21.

TABLE 2

| Ex. # | R⁵ = | MS (FAB) or HRMS (FAB) calculated for | Found: |
|---|---|---|---|
| 22 | (sugar structure) | $C_{64}H_{84}N_7O_{20}$: 1270.5771. | 1270.5763 (M + H). |
| 23 | (disaccharide structure) | $C_{70}H_{94}N_7O_{25}$: 1432.6. | 1432.9 (M + H). |
| 24 | (sugar structure) | $C_{64}H_{84}N_7O_{20}$: 270.5771. | 1270.5801 (M + H). |
| 25 | (methyl ester sugar structure) | $C_{65}H_{83}N_7O_{21}$: 1297. | 1322.5 (M + Na). |
| 26 | (deoxy sugar structure) | $C_{64}H_{83}N_7O_{19}$: 1254.4. | 1254 (M + H). |
| 27 | (deoxy sugar structure) | $C_{64}H_{83}N_7O_{19}$: 1254.4. | 1254.7 (M + H). |
| 28 | (deoxy sugar structure) | $C_{64}H_{83}N_7O_{19}$: 1254.4. | 1254.7 (M + H). |

TABLE 2-continued

| Ex. # | R⁵ = | MS (FAB) or HRMS (FAB) calculated for | Found: |
|---|---|---|---|
| 29 | (sugar with OH, HO, OH, NHAc) | $C_{66}H_{86}N_8O_{20}$: 1311.5. | 1311.7 (M + H). |
| 30 | (sugar with HO, OH, OH) | $C_{63}H_{81}N_7O_{19}$: 1240.4. | 1240.7 (M + H). |
| 31 | (sugar with OH, HO, OH, NHCBz) | $C_{72}H_{90}N_8O_{21}$: 1403.6. | 1403.9 (M + H). |
| 32 | (sugar with Me, HO, OH, OH) | $C_{64}H_{84}N_7O_{19}$: 1254.5822. | 1254.5809 (M + H). |
| 33 | (sugar with OH, HO, OH, N₃) | $C_{64}H_{82}N_{10}O_{19}$: 1295.4. | 1295.8 (M + H). |
| 34 | (cyclohexane with OH, HO, OH, N₃) | $C_{64}H_{82}N_{10}O_{19}$: 1295.4. | 1295.5 (M + H). |
| 35 | (sugar with Me, HO, OH, N₃) | $C_{64}H_{82}N_{10}O_{18}$: 1279.4. | 1279.5 (M + H). |

TABLE 2-continued

| Ex. # | $R^5 =$ | MS (FAB) or HRMS (FAB) calculated for | Found: |
|---|---|---|---|
| 36 | (azido-methyl pyranose structure with $N_3$, HO, OH, OH) | $C_{64}H_{82}N_{10}O_{19}$: 1295.4. | 1334.4 (M + K). |
| 37 | (methyl pyranose structure with Me, HO, OH, OH) | $C_{64}H_{83}N_7O_{19}$: 1254.4. | 1254.5 (M + H). |
| 38 | (pyranose structure with OH, HO, OH, $N_3$) | $C_{64}H_{82}N_{10}O_{19}$ 1295.4. | 1295.5 (M + H). |
| 39 | (pyranose structure with HO, OH, OH) | | |

Example 40

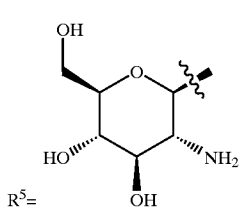

The compound of Example 31 (709.2 mg, 0.505 mmol) was dissolved in 75 mL ethanol with 0.7 g of 10% palladium on carbon under an atmosphere of hydrogen at 60 psi for 4 hours at room temperature in a Parr apparatus. The palladium on carbon was filtered off and the ethanol was removed in vacuo to yield a white solid. Purification via reverse phase HPLC yielded 201.4 mg (31.3%) of the title compound. HRMS(FAB) calculated for $C_{64}H_{85}N_8O_{19}$ (M+H): 1269.5949. Found: 1269.5931.

Example 41

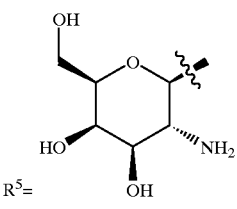

A 25 mL round bottom flask was charged with the compound of Example 34 (52.5 mg, 0.04 mmol) and nickel chloride hexahydrate (54.5 mg, 0.229 mmol) in 5 mL of anhydrous methanol at 0° C. Sodium borohydride (27.1 mg, 0.72 mmol) was then added to the reaction mixture. The reaction was raised to room temperature and allowed to stir for 2 hours. The reaction was quenched with 2 drops of 1M aqueous hydrochloric acid. The reaction mixture was filtered and the product was isolated via reverse phase HPLC to yield 20.6 mg of the title compound as a white solid. (40.0%). HRMS(FAB) calculated for $C_{64}H_{85}N_8O_{19}$ (M+H): 1269.5949. Found: 1269.5931.

Example 42

R⁵=

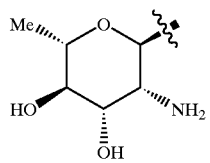

The compound of Example 35 was converted to the title compound by the procedure of Examples 41. HRMS(FAB) calculated for $C_{64}H_{85}N_8O_{18}$ (M+H): 1253.5982. Found: 1253.5995.

Example 43

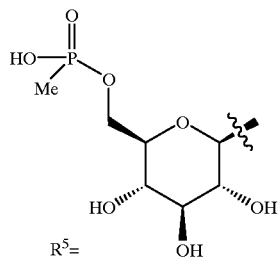

The compound of Example 21 (53.0 mg, 0.042 mmol) was placed in a 25 mL round bottom flask and dissolved in 5 mL tetrahydrofuran at 0° C. Lithium hexamethyldisilazane (0.040 mmol) was then added dropwise to the reaction mixture. The reaction was allowed to stir for 0.5 hours at 0° C. upon which time methyl phosphonic dichloride (excess) was added. The reaction mixture was raised to room temperature and allowed to stir for 1.5 hours. The reaction was quenched with 5 drops of water and the solvent was removed in vacuo. The title compound was isolated via reverse phase HPLC as a white solid (24.2 mg, 41.7%) after lyophilization. MS(FAB) calculated for $C_{65}H_{86}N_7O_{24}P$ (M+Li): 1386.6. Found: 1385.8.

Examples 44 and 45 have the following base structure and were prepared by the procedure of Examples 1 and 21 respectively.

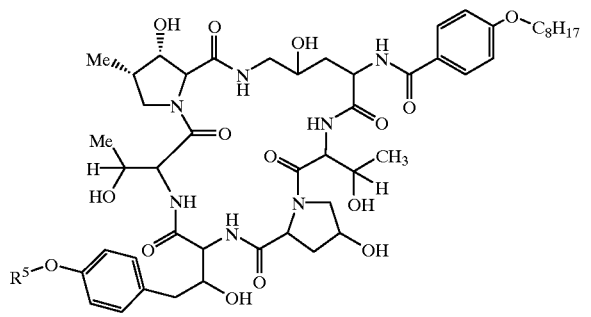

Example 44

R⁵=

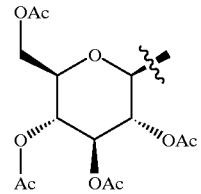

Example 45

R⁵=

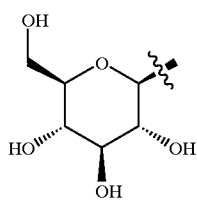

MS (FAB) calculated for $C_{55}H_{81}N_7O_{20}$ (M+H): 1159.5. Found: 1160.6.

The compounds of formula I exhibit antifungal and antiparasitic activity. For example, the compounds of formula I inhibit the growth of various infectious fungi including Candida spp. such as *C. albicans, C. parapsilosis, C. krusei, C. glabrata,* or *C. tropicalis, C. lusitaniae;* Torulopus spp. such as *T. glabrata;* Aspergillus spp. such as *A. fumigatus;* Histoplasma spp. such as *H. capsulatum;* Cryptococcus spp. such as *C. neoformans;* Blastomyces spp. such as *B. dermatitidis;* Fusarium spp., Trichophyton spp., *Pseudallescheria boydii, Coccidioides immitis, Sporothrix schenckii* and the like.

Antifungal activity of a test compound is determined in vitro by obtaining the minimum inhibitory concentration (MIC) of the compound using a standard agar dilution test or a disc-diffusion test. The compound is then tested in vivo (in mice) to determine the effective dose of the test compound for controlling a systemic fungal infection.

Accordingly, representative compounds of the present invention were tested for, and displayed, antifungal activity against at least one of the following fungii: *C. albicans, C. parapsilosis, C. neoformans,* Histoplasma spp, and *A. fumigatus.*

The compounds of the invention also inhibit the growth of certain organisms primarily responsible for opportunistic infections in immunosuppressed individuals. For example, the compounds of the invention inhibit the growth of *Pneumocystis carinii* the causative organism of pneumocystis pneumonia (PCP) in AIDS and other immunocompromised hosts. "Topley and Wilson's Microbiology and Microbial Infections," Vol. 5, Ch. 22, Oxford University Press, Inc., New York, N.Y., 1998. Other protozoans that are inhibited by compounds of formula I include Plasmodium spp., Leishmania spp., Trypanosoma spp., Cryptosporidium spp., Isospora spp., Cyclospora spp., Trichomonas spp., Microsporidiosis spp. and the like.

Administration/Formulation

The dose of the compound of formula I administered will vary depending on such factors as the nature and severity of the infection, the age and general health of the host and the tolerance of the host to the antifungal agent. The particular dose regimen likewise may vary according to such factors and may be given in a single daily dose or in multiple doses during the day. The regimen may last from about 2–3 days to about 2–3 weeks or longer. A typical daily dose (administered in single or divided doses) will contain a dosage level of from about 0.01 mg/kg to about 100 mg/kg of body weight of an active compound of this invention. Preferred daily doses generally will be from about 0.1 mg/kg to about 60 mg/kg and ideally from about 2.5 mg/kg to about 40 mg/kg.

A compound of formula I may be administered parenterally, for example using intramuscular, subcutaneous, or intra-peritoneal injection, nasal, or oral means. In addition to these methods of administration, a compound of formula I may be applied topically for skin infections.

The present invention also provides pharmaceutical formulations useful for administering the antifungal compounds of the invention. The active ingredient in such formulations comprises from 0.1% to 99.9% by weight of the formulation, more generally from about 10% to about 30% by weight.

For parenteral administration the formulation comprises a compound of formula I and a physiologically acceptable diluent such as deionized water, physiological saline, 5% dextrose and other commonly used diluents. The formulation may contain a solubilizing agent such as a polyethylene glycol or polypropylene glycol or other known solubilizing agent. Such formulations may be made up in sterile vials containing the antifungal and excipient in a dry powder or lyophilized powder form. Prior to use, a physiologically acceptable diluent is added and the solution withdrawn via syringe for administration to the host.

The present pharmaceutical formulations are prepared by known procedures using known and readily available ingredients. In making the compositions of the present invention, the active ingredient will generally be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups; aerosols, (as a solid or in a liquid medium), ointments containing, for example, up to 10% by weight of the active compound, soft and hard gelatin capsules, suppositories, sterile injectable solutions, sterile packaged powders and the like.

For oral administration, the antifungal compound is filled into gelatin capsules or formed into tablets. Such tablets may also contain a binding agent, a dispersant or other suitable excipients suitable for preparing a proper size tablet for the dosage and particular antifungal compound of the formula I. For pediatric or geriatric use the antifungal compound may be formulated into a flavored liquid suspension, solution or emulsion. A preferred oral formulation is linoleic acid, cremophor RH-60 and water and preferably in the amount (by volume) of 8% linoleic acid, 5% cremophor RH-60, 87% sterile water and a compound of formula I in an amount of from about 2.5 to about 40 mg/mL.

For topical use the antifungal compound may be formulated with a dry powder for application to the skin surface or it may be formulated in a liquid formulation comprising a solubilizing aqueous liquid or non-aqueous liquid, e.g., an alcohol or glycol.

The following formulation examples are illustrative only and are not intended to limit the scope of the invention in any way. The term "active ingredient" means a compound of formula I or a pharmaceutical salt thereof.

Formulation Example 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation Example 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

|  | Weight |
| --- | --- |
| Active ingredient | 0.25 |
| Ethanol | 25.75 |
| Propellant 22 (Chlorodifluoromethane) | 74.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation Example 4

Tablets, each containing 60 mg of active ingredient, are made as follows:

| Active ingredient | 60.0 mg |
| --- | --- |
| Starch | 45.0 mg |

-continued

| | |
|---|---|
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 150.0 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation Example 6

Suppositories, each containing 225 mg of active ingredient, are made as follows:

| | |
|---|---|
| Active ingredient | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient per 5 mL dose, are made as follows:

| | |
|---|---|
| Active ingredient | 50 mg |
| Sodium carboxymethyl cellulose | 50 mg |
| Syrup | 1.25 mL |

-continued

| | |
|---|---|
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

An intravenous formulation may be prepared as follows:

| | |
|---|---|
| Active ingredient | 100 mg |
| Isotonic saline | 1,000 mL |

The solution of the above ingredients generally is administered intravenously to a subject at a rate of 1 mL per minute.

We claim:

1. A method of inhibiting fungal activity comprising administering to a host in need of such inhibition an effective amount of a compound of formula I

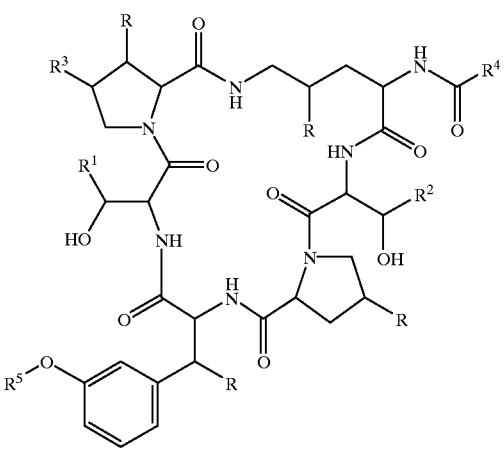

wherein

R is independently at each occurrence hydrogen, hydroxy, or O—Pg;

$R^1$ is hydrogen, methyl, $CH_2C(O)NH_2$, $CH_2C(O)NH$—Pg;

$R^2$ and $R^3$ are independently hydrogen or methyl;

$R^4$ is a moiety of the formula

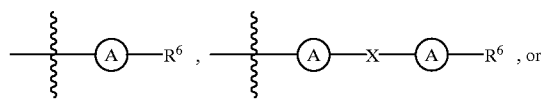

-continued

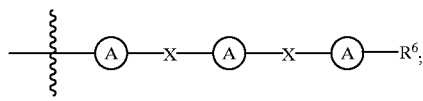

$R^5$ is a moiety of the formula

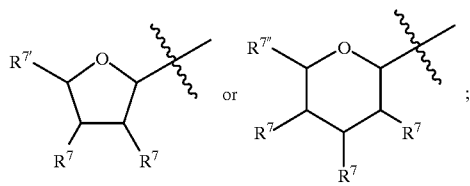

A is independently at each occurrence phen-di-yl, pyridin-di-yl, pyridazin-di-yl, pyrimidin-di-yl, pyrazin-di-yl, furan-di-yl, or thiophen-di-yl rings;

X is independently at each occurrence a bond or C≡C;

$R^6$ is hydrogen, $C_1$–$C_{12}$ alkyl, $C_2$–$C_{12}$ alkynyl, $C_1$–$C_{12}$ alkoxy, $C_1$–$C_{12}$ alkylthio, halo, or —O—$(CH_2)_m$—[O—$(CH_2)_n$]$_p$—($C_1$–$C_{12}$ alkyl), or —O—$(CH_2)_q$—Z—$R^8$;

$R^7$ is independently at each occurrence hydrogen, hydroxy, amino, azido, $OR^5$, O—Pg, or $NH_p$—Pg;

$R^{7'}$ is $CHR^7CH_2R^7$, $CHR^7CH_2OR^9$, ethyl, $CHR^7CO_2H$, $CHR^7CH_2O$—Pg, or $CHR^7C(O)$—Pg;

$R^{7''}$ is hydrogen, $CH_2R^7$, $CH_2OR^9$, methyl, $CO_2H$, $CH_2O$—Pg, $CH_2NH_p$—Pg, or C(O)—Pg;

m, n, and q are independently 2, 3 or 4;

p is 0 or 1;

Z is pyrrolidin-di-yl, piperidin-di-yl, or piperazin-di-yl;

$R^8$ is hydrogen, $C_1$–$C_{12}$ alkyl, benzyl, or substituted $C_3$–$C_{12}$ cycloalkylmethyl;

$R^9$ is $SO_3H$ or a moiety of the formula

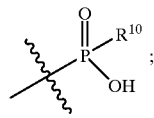

$R^{10}$ is hydroxy, $C_1$–$C_6$ alkyl, $C_1$–$C_6$ alkoxy, phenyl, phenoxy, p-halophenyl, p-halophenoxy, p-nitrophenyl, p-nitrophenoxy, benzyl, benzyloxy, p-halobenzyl, p-halobenzyloxy, p-nitrobenzyl, or p-nitrobenzyloxy; and Pg is a hydroxy, amino, amido or carboxy protecting group; with the proviso that the total number of $R^7$ substituents that are $OR^5$ groups does not exceed two; or a pharmaceutical salt or solvate thereof.

2. The method of claim 1 wherein the compound of formula I is a compound wherein R is hydroxy at each occurrence;

$R^1$, $R^2$, and $R^3$ are each methyl; and $R^4$ is a moiety of the formula

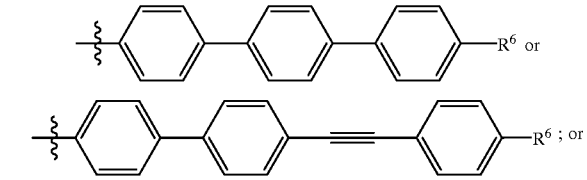

a pharmaceutically acceptable salt or solvate thereof.

3. The method of claim 2 wherein $R^4$ is a moiety of the formula

$R^5$ is a moiety of the formula

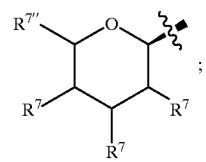

$R^6$ is hydrogen or $C_3$–$C_7$ alkoxy;

$R^7$ is independently at each occurrence hydrogen, hydroxy, amino, or $OR^5$; and $R^{7''}$ is hydrogen, $CH_2R^7$, $CH_2OR^9$, methyl, $CO_2H$, or C(O)—Pg; or a pharmaceutical salt or solvate thereof.

4. The method of claim 3 wherein $R^6$ is n-pentoxy;

$R^7$ is independently at each occurrence hydroxy or amino;

$R^{7''}$ is hydrogen, hydroxymethyl, $CH_2OR^9$, methyl, or $CO_2Me$; and $R^9$ is a moiety of the formula

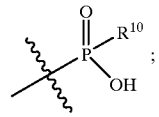

or a pharmaceutical salt thereof.

5. The method of claim 4 wherein $R^7$ is independently at each occurrence hydroxy;

$R^{10}$ is $C_1$–$C_4$ alkyl; or a pharmaceutical salt thereof.

6. The method of claim 1 wherein the fungal activity arises from a fungi selected from the group consisting of *Candida albicans, Aspergillus fumigatis, Candida parapsilosis* and combinations thereof.

* * * * *